(12) United States Patent
Ireland

(10) Patent No.: US 11,185,692 B2
(45) Date of Patent: Nov. 30, 2021

(54) LIGHT TOUCH THERAPEUTIC HEADSET

(71) Applicant: Emily Ireland, New York, NY (US)

(72) Inventor: Emily Ireland, New York, NY (US)

(73) Assignee: Emily Ireland, Lawrence, NJ (US)

( * ) Notice: Subject to any disclaimer, the term of this patent is extended or adjusted under 35 U.S.C. 154(b) by 126 days.

(21) Appl. No.: 16/708,617

(22) Filed: Dec. 10, 2019

(65) Prior Publication Data

US 2020/0108250 A1    Apr. 9, 2020

Related U.S. Application Data

(60) Provisional application No. 62/735,085, filed on Oct. 31, 2018.

(51) Int. Cl.
*A61N 1/36* (2006.01)
*A61N 1/04* (2006.01)

(52) U.S. Cl.
CPC ....... *A61N 1/36036* (2017.08); *A61N 1/0476* (2013.01); *A61N 1/36025* (2013.01)

(58) Field of Classification Search
CPC ............ A61N 1/36036; A61N 1/36025; A61N 1/0476; A61N 1/36034; A61N 1/0456; A61H 2201/1604; A61H 2201/5097; A61H 2201/165; A61H 2201/0157; A61H 2205/027; A61H 2201/5025; A61H 39/002
See application file for complete search history.

(56) References Cited

U.S. PATENT DOCUMENTS

| | | | |
|---|---|---|---|
| 2005/0052630 A1* | 3/2005 | Smith ................... | A61N 1/327 355/53 |
| 2005/0165460 A1* | 7/2005 | Erfan ................... | A61N 1/0472 607/57 |
| 2017/0224990 A1* | 8/2017 | Goldwasser ......... | A61N 1/0456 |
| 2018/0200522 A1* | 7/2018 | Taca, Jr. ............. | A61N 1/36089 |

* cited by examiner

*Primary Examiner* — Amanda K Hulbert
*Assistant Examiner* — Natasha Patel

(57) ABSTRACT

The present invention discloses a wireless and self-contained headset that delivers an electronic signal to a precise and self-locating position within bilateral conchae in both ears of a human user. The headset comprises an electronics housing that carries a specific waveform source. The waveform source generates the electronic signal, which is delivered simultaneously to both left and right ears of the human user. An array of silver electrodes housed within the bilateral earpieces cover with precision the location at the exact center of the relatively smooth plane of the conchae directly behind the external auditory meatus (ear opening/canal).

10 Claims, 5 Drawing Sheets

LIGHT TOUCH THERAPEUTIC HEADSET

CROSS-REFERENCE TO RELATED PATENT DOCUMENTS

This patent application claims the benefit of priority of U.S. Provisional Application No. 62/735,085 entitled "LIGHT TOUCH THERAPEUTIC HEADSET," filed Oct. 31, 2018, which are hereby incorporated herein by reference in its entirety.

FIELD OF THE INVENTION

The present application generally relates to treatment devices, and more particularly to a light touch therapeutic headset for facilitating electrotherapy for treating heroin addiction. The purpose of this invention is not to replace any kind of therapy or other type of treatment. Instead, the purpose of the present invention is rather to enhance effectiveness of such therapies and treatments in case of heroin addiction. Any patient will be more receptive to other therapies as well as rehabilitative methods such as support groups, psychological counseling, family and community support, or the like, when treated with electrotherapy using the light touch therapeutic headset of the present invention.

BACKGROUND

Generally, the physical condition of a human is reflected on the human's ears. The reflection by the ears, as hypothesized and demonstrated, was in inverted fetus in the fetal position. The physical conditions reflected by the ears are indicated by small areas of electrical resistance which are different from that of the immediate surroundings on the ear. These small areas, which are referred to as "conchae," can be of a higher or lower resistance, than the immediate surroundings. Points of high resistance are referred to as positive points and points of low resistance are referred to as negative points. It has been established that when the centers of positive points are inundated with electrical pulses having a higher potential at the centers of the points, the points return to resistive equibalance with the surroundings after a period of time. The return of the point to resistive equibalance causes the human's body to return to a normal homeostasis. Also, the various portions of the ears and, therefore, the human's body return to homeostasis or equibalance at variant frequencies and intensities of the applied pulses. Thus, by performing treatment using variant frequencies and intensities over specific points of the conchae of the ears, specific addictions such as heroin addiction may be optimized.

Given the unique characteristics of heroin addiction, most notably the feeling of ultimate joy when using the drug compared to the feeling of deepest agony when not using, the present device has been built with the intention to provide treatment for heroin users, rather than a more general population of all opioid users. Specific personality traits have also been demonstrated by the heroin users, evidenced in studies which detail the extreme emotional conditions that the heroin users experience, and the specific response to the drug, as well as a specific response to the absence of the drug. Research has shown that heroin addicts tend to have specific personality qualities, distinguished from those of other addiction disorders. People who become addicted to heroin tend to be highly sensitive, vulnerable to stress, sensorially overloaded, and perhaps therefore, socially introverted, all of which leads to feelings of loneliness and hopelessness.

Since 1974, the NADA (National Acupuncture Detoxification Association) protocol, which is a system of ear acupuncture, has been used as an addiction treatment. It is based on the findings of Dr. H. L. Wen, while administering his protocol of electro-acupuncture treatments as a neurosurgical consultant in Hong Kong in 1972. Over 100 cases of heroin addiction were followed by Dr. Wen, all of whom received a 100% success rate in getting off their drug without any medications. Effects were immediate in the form of elimination of withdrawal symptoms, as well as the complete loss of desire for heroin. When a few patients did experience acute withdrawal symptoms, such symptoms were gone after 20 minutes of treatment. After 40 minutes, the effect was a loss of desire for heroin. After 10 days, patients reported they had completely lost the desire for heroin.

The treatment of drug addiction in the United States, including that of heroin addiction, was altered by American practitioners in the formation of the NADA protocol, which consists of a series of 5 auricular points. These acupuncture points were added or changed from the original discovery of Dr. Wen and the revised treatment has been conducted upon a large group of vulnerable patients since the 1970's. The objective became to "detox," or to remove the effects of addictive substances from the brain.

However, this is not what the original founder of the treatment method had discovered. Dr. Wen provided electrostimulation to one auricular point only. The underlying mechanism was presumed to be the re-conditioning of the brain, not detoxification. These are highly significant results, especially given the extremes to which heroin addicts will go to get the drug, and how desperately in agony they feel when they do not have it, along with the countless lives of individuals, friends and family members who are affected by each person's addiction disorder. Therefore, it is this inventor's intention that electrostimulation for heroin addiction, without needle insertion (which, unlike the NADA protocol, prevents the risk of needle-carrying disease), on a single ear location be available to the general population for personal or clinical use.

There are several prior arts that disclose the similar device as described in the present invention. For example, US patent publication number 20050165460 discloses a self-contained, portable headset that carries a waveform source device and tissue interface circuits in a self-locating position for delivering treatment signals to a preselected area in the conch of the ear of a human subject. An electronics housing carries a waveform source device in communication with tissue interface circuits, carried respectively in earpiece housings. The headset carries each earpiece housing at a rearward and downward angle so that a protruding trunk enters the conch of the outer ear and contacts the conch generally below and rearwardly of the ear canal. An audio speaker delivers associated tones during treatment. An end wall of the trunk carries an array of electrodes contacts the preselected area in the conch of the ear. These examples from the prior art show that devices have been designed for generating waveforms of many varied types. The devices vary frequency, amplitude, and other characteristics of the waveform. Both digital and analog waveforms have been created, can be stored for replication, and can be converted between digital and analog modes. These devices still can be large and complex to administer. Smaller devices are known, but they are limited in their ability to provide coordinated stimulation at both ears. Thus, it would be desirable to improve the performance of the known devices in order to provide more effective, proven treatments to users with heroin addiction. In particular, it would be desirable to create an improved portable treatment device that the patient can carry and apply to himself, both for introductory usage and for subsequent usage. Such an effective, portable, and self-applied device enables the patient to treat himself at unpredictable, critical times when his condition recurs.

SUMMARY

It will be understood that this disclosure is not limited to the particular systems and methodologies described herein, as there can be multiple possible embodiments of the present disclosure which are not expressly illustrated in the present disclosure. It is also to be understood that the terminology used in the description is for the purpose of describing the particular versions or embodiments only and is not intended to limit the scope of the present disclosure.

It is an objective of the present invention to provide a light touch therapeutic headset for facilitating electrotherapy for treating heroin addiction.

In an embodiment, the wireless and self-contained headset delivers an electronic signal to a precise and self-locating position within bilateral conchae in both ears of a human user. The headset comprises an electronics housing that carries a specific waveform source. The waveform source generates the electronic signal, which is delivered simultaneously to both left and right ears of the human user. An array of silver electrodes housed within the bilateral earpieces cover with precision the location at the exact center of the relatively smooth plane of the conchae directly behind the external auditory meatus (ear opening/canal).

While similar devices have been made in the past, the exceptions to the headset device disclosed in the present invention lie in the following changes and improvements:

1. The variability or range of frequency does not change i.e., the frequency is invariable and never wavers but is constant.
2. The constant or invariable frequency level is set at 90 cycle per second (cps) and does not change.
3. The waveform source is unmodulated and does not change.
4. The square pulse waveform is unmodulated.
5. There are not any auditory signals, or sounds of any kind, such as music or tones, emitted from this device.
6. Any design changes or additions including, but not limited to, color schemes, patterns, gemstone overlays, or the like are unique to this device.
7. This device is built with intention to cure heroin users of their addiction, and is not targeted towards any other group or subcategory of addicted or stressed individuals, such as any other type of narcotics user, any type of smoker, headache/migraine, PMS, insomnia, bereavement, PTSD, stress or anxiety patient but rather can be used in such cases, without the intention to cure any other addictions or stress problems other than that of heroin.
8. This device does not require any type of training to use. It can be used by anyone who can pick up the device and place it on the ears, or if the case may be, on one's own head, with little instruction other than to turn it on and place it upon the head of the user who needs treatment.
9. This device is completely self-locating, unlike previously made devices, which require minimal to extensive training to use with successful results. This device does not require any preparation, knowledge or skills other than the ability to place it on the head of the user in need of help, and to turn the device's power switch to the ON position. Because it is a self-locating mechanism, anyone can use it with accuracy.
10. The recommended amount of time for usage is 40 minutes per day for a duration of 10 days, although it may also be used overnight, and is designed comfortably enough to be worn during sleep, or for greater amounts of time. The device can be used with significant observable results within the first 30 minutes. There is no maximum treatment time as the device can be worn up to 6 hours per day or longer, even to sleep in.

The purpose of this invention is not to replace any kind of therapy or other type of treatment, but rather to enhance the effectiveness of such therapies and treatments in the case of heroin addiction. The patient (i.e., the human user who is addicted to heroin) may be more receptive to other therapies as well as rehabilitative methods such as support groups, psychological counseling, family and community support, or the like, when treated with electrotherapy using the light touch therapeutic headset device of the present invention.

Neurochemical in its immediate effects, a process of brain re-conditioning, occurs over the long-term course of treatment. The use of this device also prevents, or stops, withdrawal symptoms.

These and other features and advantages of the present invention will become apparent from the detailed description below, in light of the accompanying drawings.

BRIEF DESCRIPTION OF ACCOMPANYING DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of various examples. It is expressly understood, however, that the drawings are for the purpose of illustration and description only and are not intended as a definition of the limits of the invention. Embodiments of this invention will now be described by way of example in association with the accompanying drawings in which:

Figure 4:
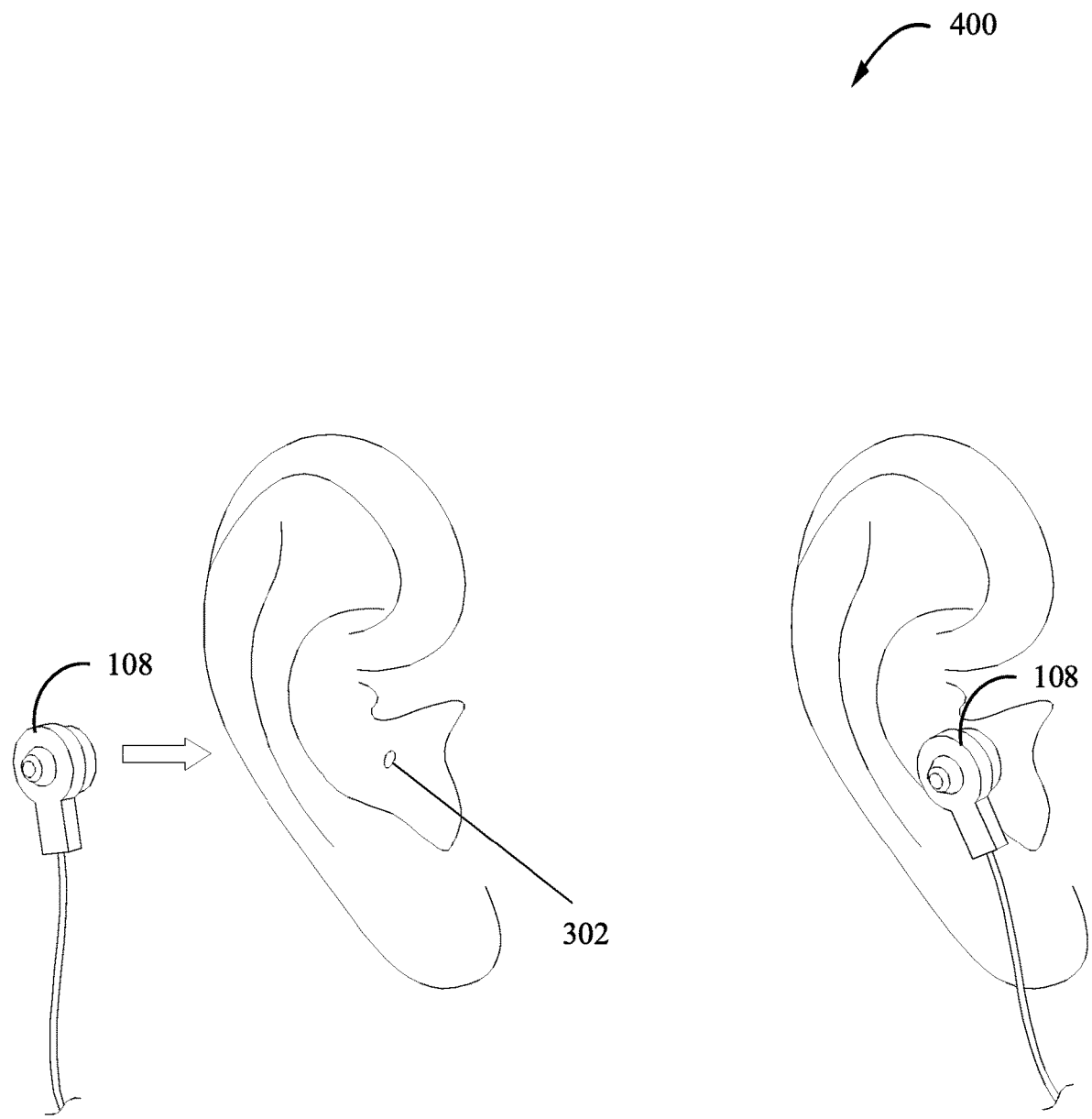
Figure 5:
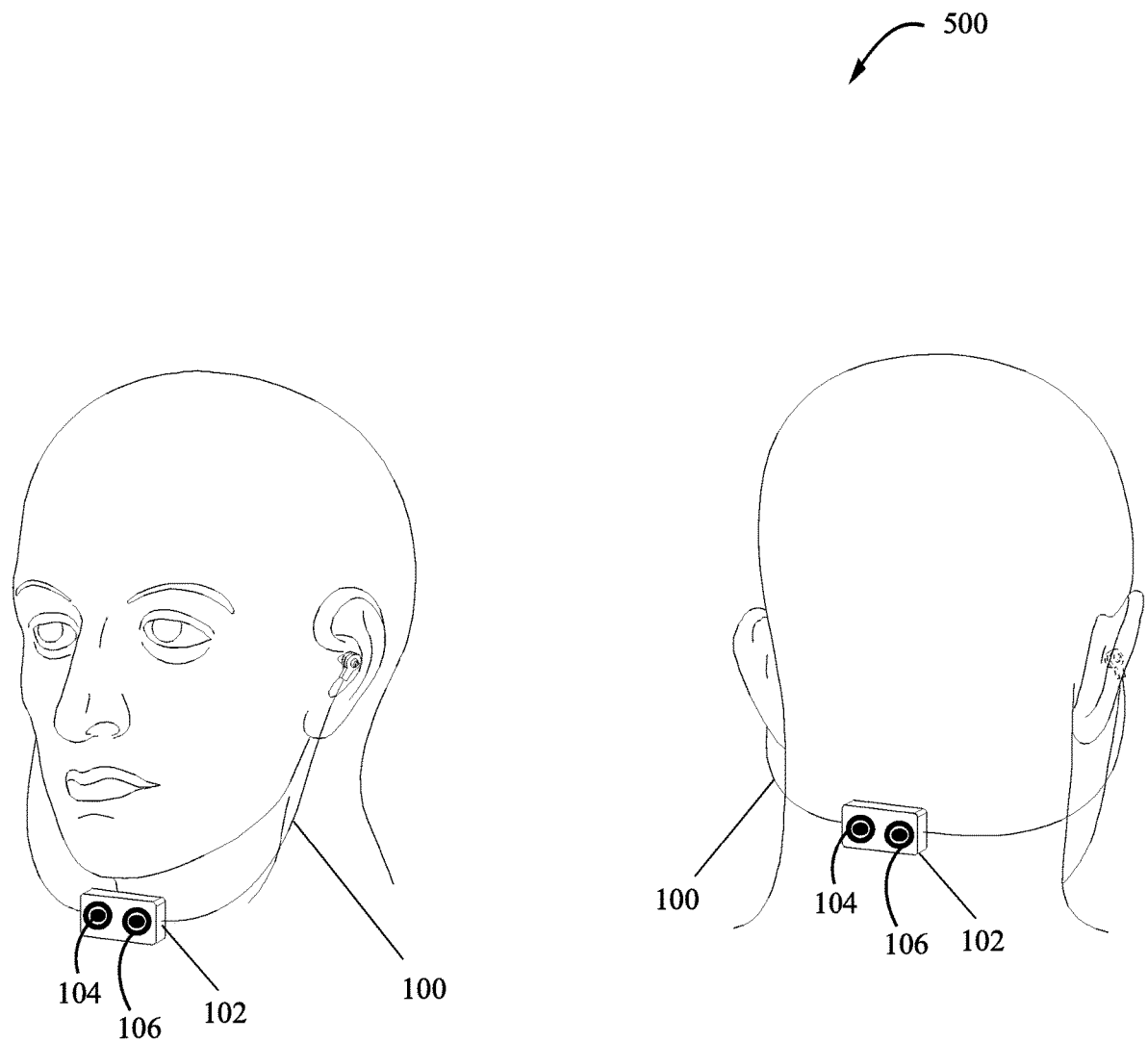

FIG. 4 is a diagram that illustrates an exemplary scenario for inserting the therapeutic headset device into the precise location area in the ear of the user desired for treatment, according to an exemplary embodiment of the present invention; and FIG. 5 is a diagram that illustrates an exemplary scenario of the user with the therapeutic headset device into the precise location area in the ear of the user desired for treatment, according to an exemplary embodiment of the present invention.

DETAILED DESCRIPTION

As used in the specification and claims, the singular forms "a", "an" and "the" may also include plural references. For example, the term "an article" may include a plurality of articles. Those with ordinary skill in the art will appreciate that the elements in the figures are illustrated for simplicity and clarity and are not necessarily drawn to scale. For example, the dimensions of some of the elements in the figures may be exaggerated, relative to other elements, in order to improve the understanding of the present invention. There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be observed that the present invention utilizes a combination of components, which constitutes a light touch therapeutic headset device for facilitating electrotherapy for treating heroin addiction. Accordingly, the components have been represented, showing only specific details that are pertinent for an understanding of the present invention so as not to obscure the disclosure with details that will be readily apparent to those with ordinary skill in the art having the benefit of the description herein. As required, detailed embodiments of the present invention are disclosed herein; however, it is to be understood that the disclosed embodiments are merely exemplary of the present invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the present invention.

References to "one embodiment", "an embodiment", "another embodiment", "yet another embodiment", "one example", "an example", "another example", "yet another example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

The words "comprising", "having", "containing", and "including", and other forms thereof, are intended to be equivalent in meaning and be open ended in that an item or items following any one of these words is not meant to be an exhaustive listing of such item or items or meant to be limited to only the listed item or items.

The light touch therapeutic headset device of the present invention will now be described with reference to the accompanying drawings, which should be regarded as merely illustrative without restricting the scope and ambit of the present invention. The light touch therapeutic headset device has been disclosed for facilitating electrotherapy for treating heroin addiction. The purpose of this invention is not to replace any kind of therapy or other type of treatment. Instead, the purpose of the present invention is rather to enhance effectiveness of such therapies and treatments in case of heroin addiction. Any patient will be more receptive to other therapies as well as rehabilitative methods such as support groups, psychological counseling, family and community support, or the like, when treated with electrotherapy using the light touch therapeutic headset device of the present invention. Embodiments of the present invention will now be described with reference to FIGS. 1-5.

Figure 1:
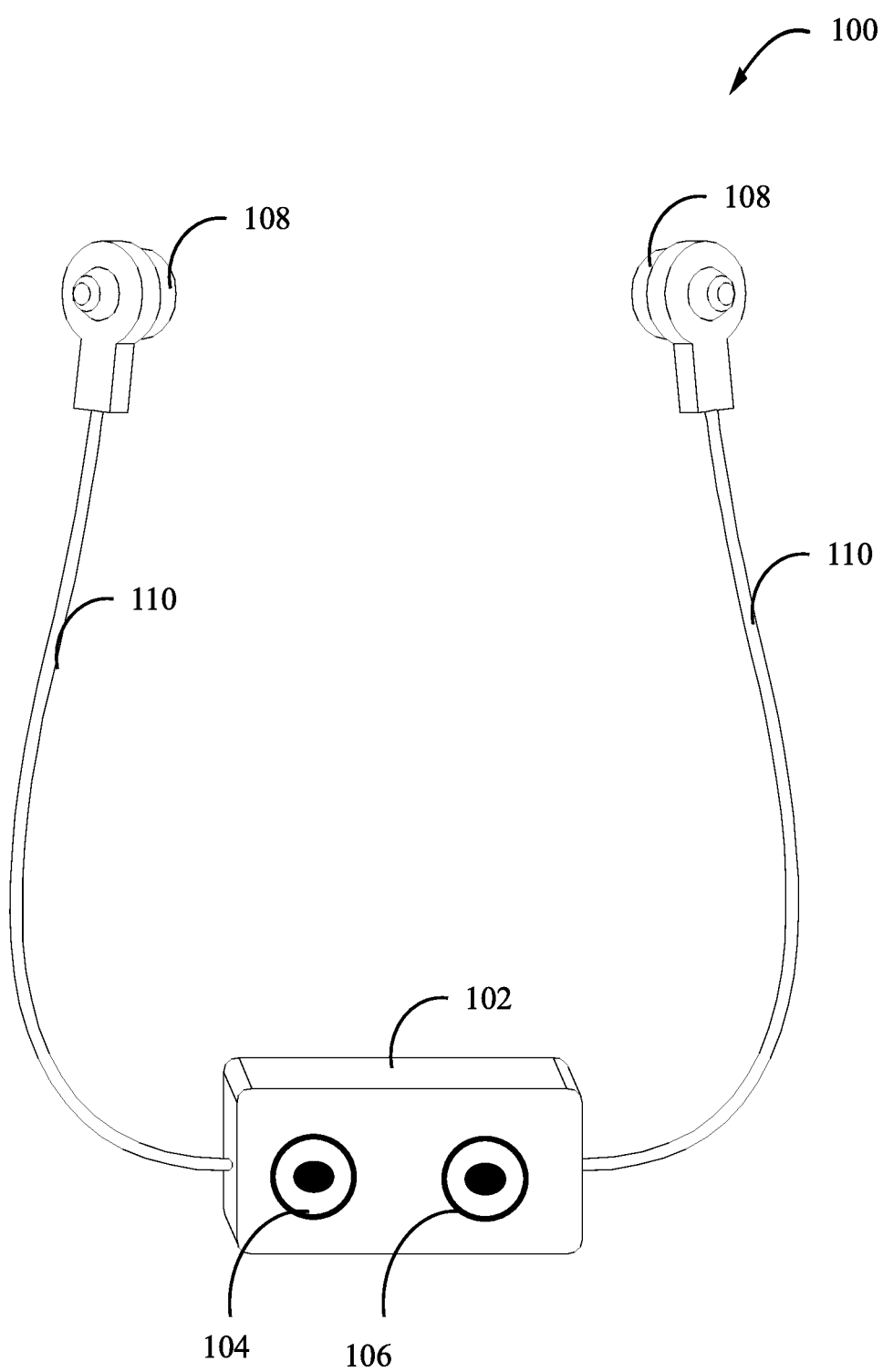
FIG. 1 is a diagram that illustrates a therapeutic headset device, according to an exemplary embodiment of the present invention.

FIG. 1 is a diagram that illustrates a therapeutic headset device 100, according to an exemplary embodiment of the present invention. The therapeutic headset device 100 includes an electronics housing 102. The electronics housing 102 includes various components such as a power switch 104 and a wireless mode switch 106. The electronics housing 102 further includes a specific waveform source (e.g., a signal generator 204 shown in FIG. 2). The waveform source generates an electronic signal, which is delivered simultaneously to both left and right ears of a human user. The therapeutic headset device 100 further includes earpiece housings 108 and headset cables 110. Each headset cable 110 is a long piece that runs from the electronics housing 102 to each earpiece housing 108. The headset cables 110 is a set of wires coated in rubber or other nonconductive material. Its job is to act as a sort of bridge along which the electronic signal from the electronics housing 102 may travel up to each earpiece housing 108.

In an embodiment, the electronics housing 102 carries the waveform source device in communication with right and left tissue interface circuits, carried respectively in right and left earpiece housings 108. The electronics housing 102 carries the waveform source device having an impedance detecting function. The right and left earpiece housings 108 are each connected to the electronics housing 102 by means of the right and left headset cables 110, respectively, and are carried in suitable positions for application, respectively, to the right and left ears of the user who is addicted with heroin. The right and left earpiece housings 108 include right and left elongated protrusions, respectively, and each extending to a respective free end wall from the right and left earpiece housings 108.

Figure 2:
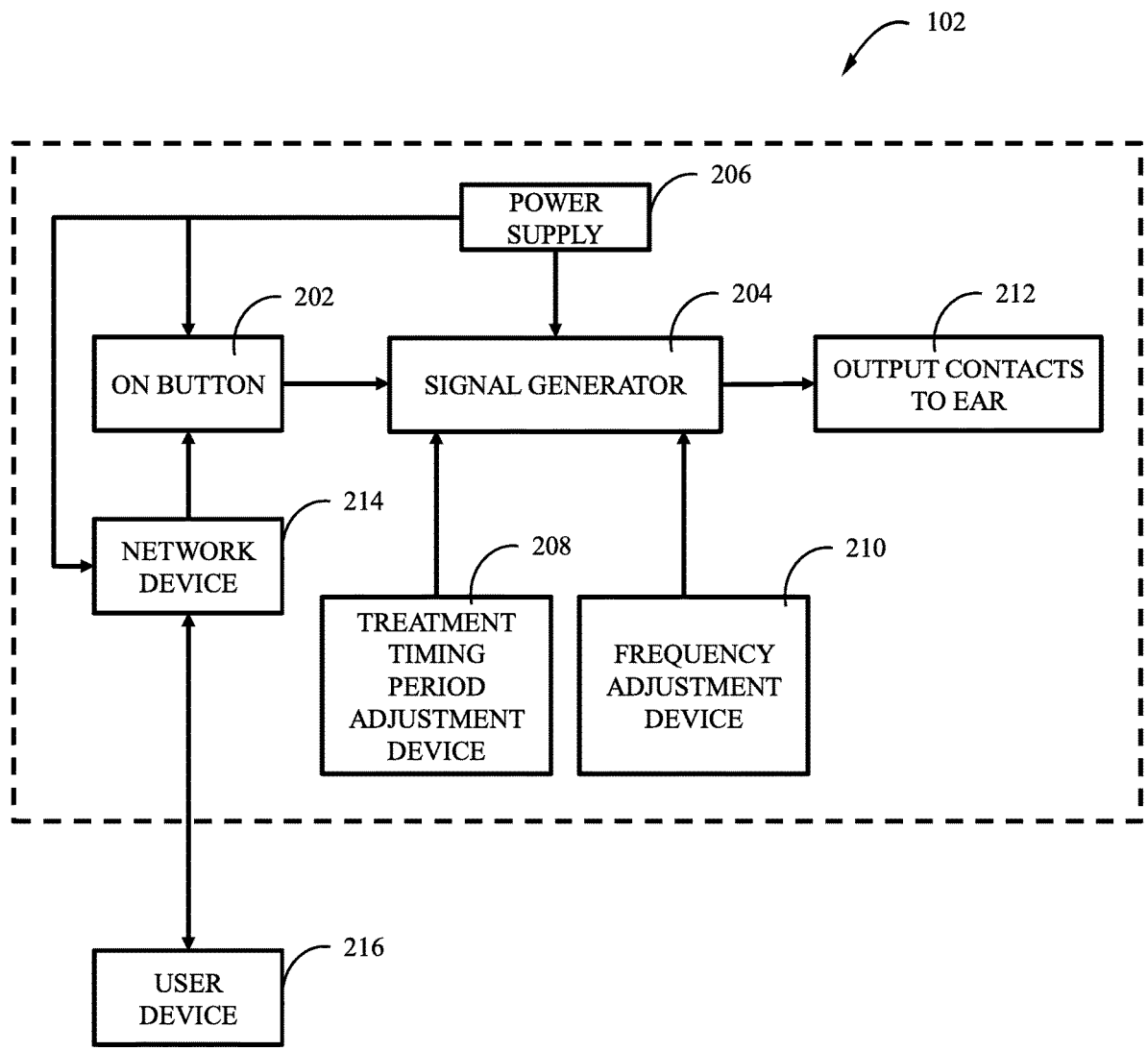
FIG. 2 is a block diagram that illustrates an electronics housing of the therapeutic headset device, according to an exemplary embodiment of the present invention.

In an embodiment, the earpiece housings 108 carry a tissue interface circuit on the free end wall, and the tissue interface circuits are in communication with the waveform source device for communicating impedance and receiving treatment signals such as the electronic signals generated by the waveform source device (i.e., the signal generator 204 shown in FIG. 2). Also, the elongated protrusions are suitably arranged for applying the respective tissue interface circuits against the conch of the ear of the user when the therapeutic headset device 100 is applied to the user. In an embodiment, the tissue interface circuit comprises an array of electrodes carried in association with the free end wall of each earpiece housing 108 and is sized to typically contact at least about one-quarter the height of the conch of the user's ear. The array is arranged to achieve electrical communication with the preselected contact areas.

In an embodiment, the therapeutic headset device 100 may be used for treating heroin addiction of the user. The purpose is not to replace any kind of therapy or other type of treatment. Instead, the purpose of the present invention is rather to enhance effectiveness of such therapies and treatments in case of heroin addiction. Any patient may be more receptive to other therapies as well as rehabilitative methods such as support groups, psychological counseling, family and community support, or the like, when treated with electrotherapy using the therapeutic headset device 100. In an embodiment, the wireless and self-contained therapeutic headset device 100 delivers the electronic signal to a precise and self-locating position within bilateral conchae in both ears of the user who is wearing the therapeutic headset device 100. The therapeutic headset device 100 comprises the electronics housing 102 that carries the specific waveform source. The waveform source generates the electronic signal, which is delivered simultaneously to both left and right ears of the user. An array of silver electrodes housed within the bilateral earpieces cover with precision the location at the exact center of the relatively smooth plane of the conchae directly behind the external auditory meatus (ear opening/canal). For efficiently and effectively performing the treatment for heroin addiction of the user, the waveform source generates the electronic signal for which variability or range of frequency does not change i.e., the frequency of the electronic signal is invariable and never wavers but is constant. In an embodiment, the constant or invariable frequency level of the electronic signal is set at 90 cycle per second (cps) or 90 Hz and does not change. Further, the waveform source is unmodulated and does not change. Further, the electronic signal is a square pulse waveform that is unmodulated. In an embodiment, there are not any auditory signals, or sounds of any kind, such as music or tones, emitted from this therapeutic headset device 100. The therapeutic headset device 100 is built with intention to cure heroin users of their addiction, and is not targeted towards any other group or subcategory of addicted or stressed individuals, such as any other type of narcotics user, any type of smoker, headache/migraine, PMS, insomnia, bereavement, PTSD, stress or anxiety patient but rather can be used in such cases, without the intention to cure any other addictions or stress problems other than that of heroin. In an embodiment, the therapeutic headset device 100 does not require any type of training to use. The therapeutic headset device 100 may be used by anyone who can pick up the device and place it on the ears, or if the case may be, on one's own head, with little instruction other than to turn it on and place it upon the head of the user who needs treatment. In an embodiment, the therapeutic headset device 100 is completely self-locating, unlike previously made devices, which require minimal to extensive training to use with successful results. This device does not require any preparation, knowledge or skills other than the ability to place it on the head of the user in need of help, and to turn the device's power switch to the ON position. Because it is a self-locating mechanism, anyone can use it with accuracy. In an embodiment, the recommended amount of time for usage is 40 minutes per day for a duration of 10 days, although it may also be used overnight, and is designed comfortable enough to be worn during sleep, or for greater amounts of time. The therapeutic headset device 100 may be used with significant observable results within the first 30 minutes. There is no maximum treatment time as the device can be worn up to 6 hours per day or longer, even to sleep in.

In an embodiment, the therapeutic headset device 100 delivers an effective electrotherapy for treating the user suffering from heroin addiction. The treatment is performed by use of the self-contained, portable, and wireless therapeutic headset device 100 that carries the selectively activated waveform source device that causes the electronic signal responsive to the measured impedance. The right and left earpiece housings 108 each carry the tissue interface circuit that is responsive to the source device to deliver unmodulated square pulse waveform. The tissue interface circuit is configured with an ear-entering portion that is suitably sized and shaped for application onto the conch of the user's ear. The ear-entering portion has a free end that carries a contact portion of the tissue interface circuit. The contact portion is an array of electrodes suitably sized and shaped for contacting the conch of the user's ear and, specifically, for contacting a preselected contact area near the lower edge of the ear canal opening and extending rearwardly from the canal. The interface circuits are applied to the ears of the user, in a position such that the tissue interface circuit is in communication with the preselected contact area (i.e., the precise and self-locating position within the bilateral conchae in both ears of the user with heroin addiction). The source device may be activated by means of the power switch 104 to provide the constant or invariable electron signal to the tissue interface circuits. As a result, the tissue interface circuits deliver an effective waveform treatment (by means of the unmodulated square pulse electronic signal that is set at 90 cps or 90 Hz) over a time period effective for heroin addiction treatment. In some embodiments, the user may activate the source device by using an application running on a user device (e.g., a smartphone) of the user. The user device may wirelessly communicate with the therapeutic headset device 100 when the user activates the wireless mode switch 106. Based on such activation, the user device and the therapeutic headset device 100 may communicate over a communication network. When communicatively connected, the user may control ON-OFF of the therapeutic headset device 100 by means of the user device. For example, the user, by means of the application running on the user device, may select an option to turn ON the waveform source (e.g., a signal generator 204 shown in FIG. 2). Based on the selection, the user device may communicate a turn ON signal to the waveform source device over the communication network. Accordingly, the waveform source device may receive the turn ON signal from the user device and generates the unmodulated square pulse electronic signal at a constant or invariable frequency of 90 cps or 90 Hz for facilitating electrotherapy for treating heroin addiction. Examples of types of the communication network may include, but are not limited to, a local area network, a wide area network, a radio network, a virtual private network, an internet area network, a metropolitan area network, a satellite network, Wi-Fi, Bluetooth Low energy, a wireless network, and a telecommunication network. Examples of the telecommunication network may include, but are not limited to, a global system for mobile communication (GSM) network, a general packet radio service (GPRS) network, third Generation Partnership Project (3GPP), an enhanced data GSM environment (EDGE), and a Universal Mobile Telecommunications System (UMTS).

FIG. 1 shows a front view of the therapeutic headset device 100 that demonstrates the position in which the headset is usually worn by the user with heroin addiction, although it may be designed in the reverse position, wrapped around the top of the head like a band as a more typical headphone set would normally be worn. However, in the position shown, it is worn hanging underneath the head and chin, fitted like a stethoscope. Sizing is adjustable to fit any user of any size or age. The electronics housing 102, which carries the waveform source, is held within the headset band.

FIG. 2 is a block diagram that illustrates the electronics housing 102 of the therapeutic headset device 100, according to an exemplary embodiment of the present invention. The electronics housing 102 includes an ON button 202, a signal generator 204, a power supply 206, a treatment timing period adjustment device 208, a frequency adjustment device 210, and output contacts 212 to the user's ear. The electronics housing 102 may further include a network device 214 for facilitating communication with a user device 216 of the user.

In an embodiment, the therapeutic headset device 100 may be turned ON by turning on the ON button 202 by means of the power switch 104. The signal generator 204 is turned on with power supplied by the power supply 206 (such as a battery). The signal generator 204 generates the electronic signal for which variability or range of frequency does not change i.e., the frequency of the electronic signal is invariable and never wavers but is constant. In an embodiment, the constant or invariable frequency level of the electronic signal is set at a frequency of 90 cycle per second (cps) or 90 Hz and does not change. Further, the waveform source is unmodulated and does not change. Further, the electronic signal is a square pulse waveform that is unmodulated. In an embodiment, there are not any auditory signals, or sounds of any kind, such as music or tones, emitted from this therapeutic headset device 100. The signal generator 204 transmits the electronic signal through the output contacts 212 to the user's ear. In an embodiment, the pattern of treatment using the constant electronic signal is adjusted for duration of treatment by means of the treatment timing period adjustment device 208 to deliver the constant or invariable frequency level of the electronic signal set at 90 cycle per second (cps) or 90 Hz over the set time periods. In an embodiment, the recommended amount of time for usage is 40 minutes per day for a duration of 10 days, although it may also be used overnight, and is designed comfortable enough to be worn during sleep, or for greater amounts of time. The therapeutic headset device 100 may be used with significant observable results within the first 30 minutes. There is no maximum treatment time as the device can be worn up to 6 hours per day or longer, even to sleep in. In an embodiment, the frequency adjustment device 210 sets the generation of the electronic signal at 90 cycle per second (cps) or 90 Hz by means of the signal generator 204.

In an embodiment, the network device 214 facilitates wireless communication between the user device 216 and the therapeutic headset device 100. The user device 216 may wirelessly communicate with the therapeutic headset device 100 when the user activates the wireless mode switch 106 to turn ON the network device 214 that facilitates the wireless communication between the user device 216 and the therapeutic headset device 100. Based on such activation, the user device 216 and the therapeutic headset device 100 may communicate over the communication network. When communicatively connected, the user may control ON-OFF of the therapeutic headset device 100 by means of the user device 216. For example, the user, by means of the application running on the user device, may select an option to turn ON the signal generator 204. Based on the selection, the user device 216 may communicate a turn ON signal to the signal generator 204 over the communication network. Accordingly, the signal generator 204 may receive the turn ON signal from the user device 216 and generates the unmodulated square pulse electronic signal at a constant or invariable frequency of 90 cps or 90 Hz for facilitating electrotherapy for treating the user with heroin addiction. Examples of types of the communication network may include, but are not limited to, a local area network, a wide area network, a radio network, a virtual private network, an internet area network, a metropolitan area network, a satellite network, Wi-Fi, Bluetooth Low energy, a wireless network, and a telecommunication network. Examples of the telecommunication network may include, but are not limited to, a global system for mobile communication (GSM) network, a general packet radio service (GPRS) network, third Generation Partnership Project (3GPP), an enhanced data GSM environment (EDGE), and a Universal Mobile Telecommunications System (UMTS).

Figure 3:
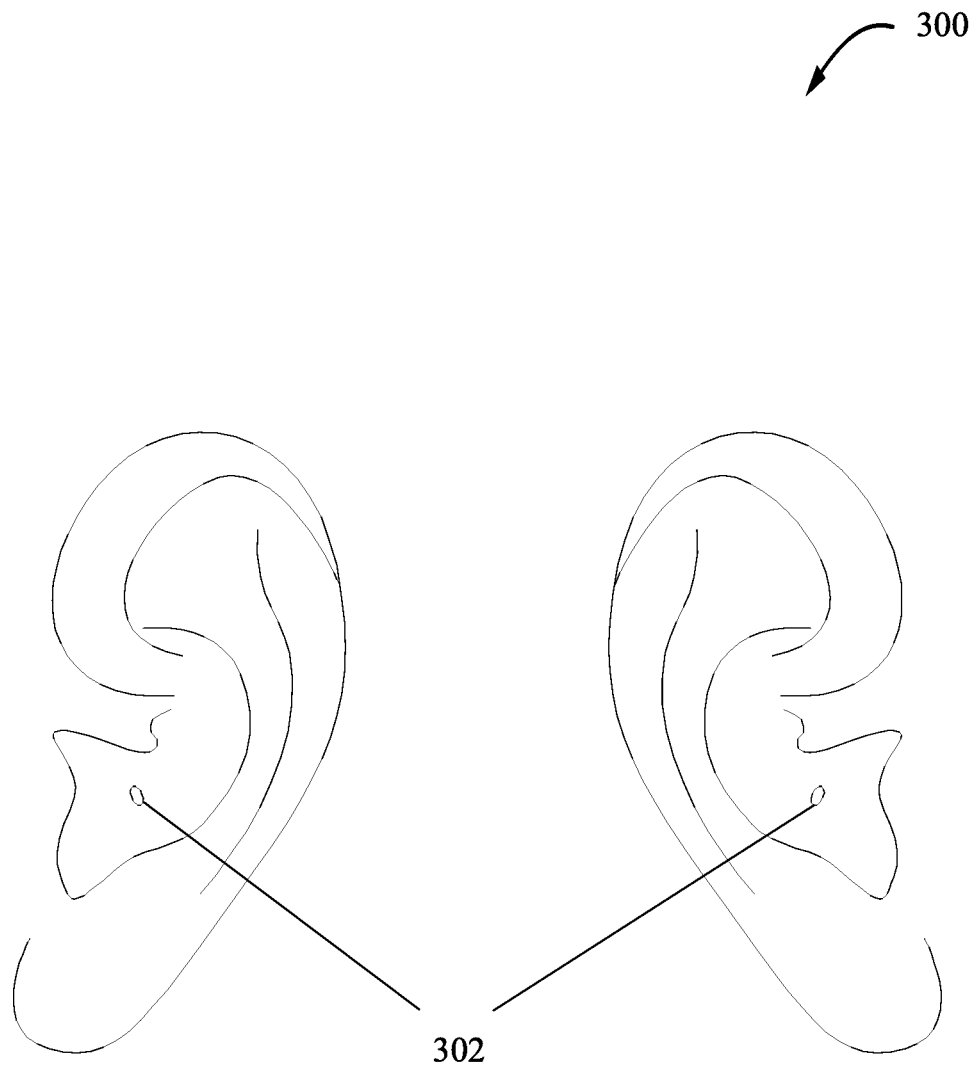
FIG. 3 is a diagram that illustrates a precise location area in an ear of a user desired for treatment, according to an exemplary embodiment of the present invention.

FIG. 3 is a diagram 300 that illustrates a precise location area 302 in an ear of the user desired for treatment for heroin addiction, according to an exemplary embodiment of the present invention. FIG. 3 demonstrates the precise location area 302 desired for the treatment. To locate on a human ear, find the smooth plane of the ear called the concha, which is located directly posterior to, or behind, each ear opening (external auditory meatus). It is firm or hard to when palpated, much like the skull when pressed with a finger, rather than the fleshier, softer parts of the ear. The location specified aligns precisely behind the center of the ear opening, directly in the center of the bilateral conchae.

FIG. 4 is a diagram 400 that illustrates an exemplary scenario for inserting the therapeutic headset device 100 into the precise location area 302 in the ear of the user desired for treatment, according to an exemplary embodiment of the present invention. In an embodiment, each earpiece housing 108 is inserted into the precise location area 302 in the ear of the user. The location specified aligns precisely behind the center of the ear opening, directly in the center of the bilateral conchae.

FIG. 5 is a diagram 500 that illustrates an exemplary scenario of the user with the therapeutic headset device 100 into the precise location area 302 in the ear of the user desired for treatment for heroin addiction, according to an exemplary embodiment of the present invention. The therapeutic headset device 100 may be worn over the head or around the user's neck hanging either in the front or rear portion of the user's head. The purpose of this invention is not to replace any kind of therapy or other type of treatment, but rather to enhance the effectiveness of such therapies and treatments in case of heroin addiction. The patient will be more receptive to other therapies as well as rehabilitative methods such as support groups, psychological counseling, family and community support, or the like. Neurochemical in its immediate effects, a process of brain re-conditioning occurs over the long-term course of treatment. The use of this device also prevents, or stops, withdrawal symptoms. The effect of neural manipulation is immediate, with complete elimination of the desire for heroin within 30 minutes, which lasts from 1 month to more than 1 year, with 0 relapses. The recommended treatment time is 40 minutes per day for 10 days, with significant observable results within the first 30 minutes. There is no maximum treatment time as the device can be worn up to 6 hours per day or longer, even to sleep in. Additional benefits include increased receptivity to and enhancement of psychotherapy, counseling, and other rehabilitative methods. The return to a normal sleep pattern, which also enhances healthy physiological functioning, mood, and rehabilitation. Improved self-esteem and mental health, including a positive outlook on life and emotional well-being. Improved motivation and ability to successfully manage daily life activities independently. Improved communication skills, comprehension, calmness and clarity of the mind. Improved physical coordination. Enhanced self-awareness. A marked decrease in depression and anxiety levels.

The present invention discloses the therapeutic headset device 100 for facilitating electrotherapy for users for treating heroin addiction. In operation, the user inserts the earpieces 108 into the precise location area 302 in the user's ear. Thereafter, the therapeutic headset device 100 is switched ON. Constant unmodulated electronic signal at 90 Hz frequency is delivered to bilateral concha region to stimulate the temporal bones and related attachments, including the articulation with the sphenoid bone, the cranial sutures and mobility of the cranial bones as they interrelate, the choroid plexus and all structures related to the cerebrospinal fluid pump mechanism, and intrinsic connective tissue. Once the user is done with each round of treatment, the device may be turned off, recharged or otherwise put away until the next use is completed. User may be sitting, lying down, standing or otherwise ambulatory in any functional activity during treatment, although for best results a restful state is recommended. Post care is not necessary, although it is advised that counseling, psychotherapy and group meetings/therapy be integrated into treatment.

Techniques consistent with the disclosure provide, among other features, the therapeutic headset device 100 for facilitating electrotherapy for users for treating heroin addiction. While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

Although particular embodiments of the invention have been described in detail for purposes of illustration, various modifications and enhancements may be made without departing from the spirit and scope of the invention. The scope of the invention is accordingly defined by the following claims.

What is claimed is:

1. A therapeutic headset device, comprising:
    an electronics housing including a waveform source for generating a constant electronic signal;
    earpiece housings; and
    headset cables,
        wherein each headset cable connects the electronics housing to each earpiece housing,
        wherein each headset cable transmits the constant electronic signal from the electronics housing to each earpiece housing that is communicated to a precise and self-locating position within bilateral conchae in each ear of a user who is wearing the therapeutic headset device for treating heroin addiction,
        wherein a frequency level of the constant electronic signal is set at 90 cycle per second (cps), and
        wherein the constant electronic signal is a square pulse waveform that is unmodulated.

2. The therapeutic headset device of claim 1, wherein the waveform source generates the constant electronic signal, which is delivered simultaneously to both left and right ears of the user.

3. The therapeutic headset device of claim 2, wherein an array of silver electrodes housed within the bilateral earpieces cover with precision a location at exact center of a relatively smooth plane of the conchae directly behind external auditory meatus.

4. The therapeutic headset device of claim 2, wherein a variability or range of frequency of the constant electronic signal does not change during the treatment of the user with the heroin addiction.

5. The therapeutic headset device of claim 4, wherein the waveform source is unmodulated and does not change.

6. The therapeutic headset device of claim 1, wherein a recommended amount of time for usage is 40 minutes per day for a duration of 10 days.

7. The therapeutic headset device of claim 1, wherein the waveform source is turned ON by means of a power switch provided on top of the electronics housing.

8. The therapeutic headset device of claim 1, wherein the waveform source is turned ON by means of an application running on a user device that is communicatively coupled to the therapeutic headset device over a communication network, when the user turns ON a wireless mode switch for communicating in a wireless manner, and wherein the wireless mode switch is provided on top of the electronics housing.

9. The therapeutic headset device of claim 6, wherein the headset device is usable with significant observable results within first 30 minutes.

10. The therapeutic headset device of claim 1, wherein the headset device delivers an effective electrotherapy for treating the user suffering from the heroin addiction.

\* \* \* \* \*